United States Patent [19]

Van de Walker et al.

[11] 4,321,998
[45] Mar. 30, 1982

[54] EARPLUG CONTAINER

[75] Inventors: Roger Van de Walker, El Toro; Weston E. Draper, Jr., Diamond Bar, both of Calif.

[73] Assignee: Norton Company, Worcester, Mass.

[21] Appl. No.: 127,710

[22] Filed: Mar. 6, 1980

[51] Int. Cl.³ .................... B65D 83/00; A61F 11/02
[52] U.S. Cl. .................................. 206/229; 206/38; 206/363; 128/151; 128/260
[58] Field of Search ............. 206/229, 5.1, 38, 230, 206/234, 216, 363, 443, 804; 128/151, 152, 260, 263, 269; 220/212, 23.8

[56] References Cited

U.S. PATENT DOCUMENTS

| | | | |
|---|---|---|---|
| 2,393,340 | 1/1946 | Russell | 206/229 |
| 2,751,913 | 6/1956 | Wilk | 206/229 |
| 3,092,119 | 6/1963 | Gold | 206/229 |
| 3,871,372 | 3/1975 | Bivins | 128/152 |
| 4,122,841 | 10/1978 | Rock | 128/151 |

Primary Examiner—Herbert F. Ross
Attorney, Agent, or Firm—Rufus M. Franklin

[57] ABSTRACT

A combined protective case and inserter for earplugs has a cover held in a closed or an open position by a frictional backing feature, and can be reversed whereby either one of two earplug inserting means are exposed externally for the case for aiding the insertion of the earplug into a users ear.

1 Claim, 8 Drawing Figures

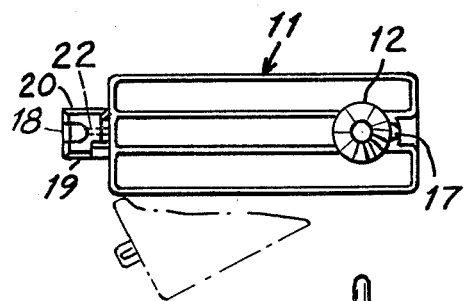
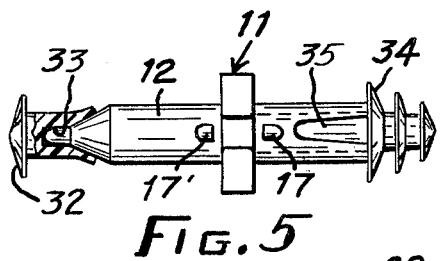
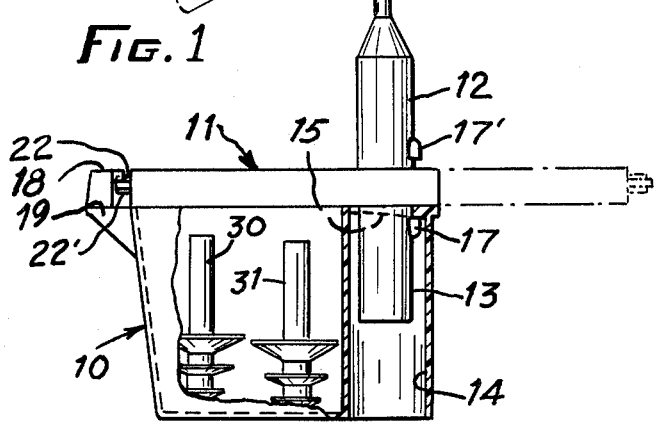
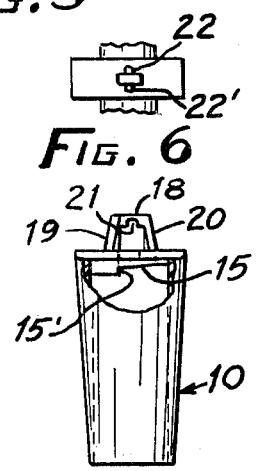
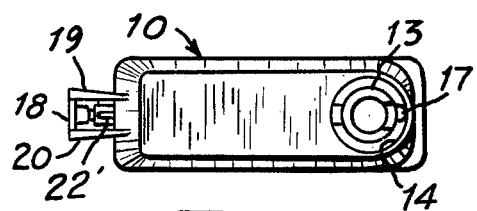
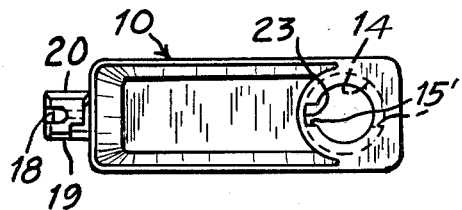
FIG. 1
FIG. 5
FIG. 6
FIG. 2
FIG. 7
FIG. 3
FIG. 4

EARPLUG CONTAINER

FIELD OF THE INVENTION

Disclosed herein is a sanitary protective case for a pair of earplugs.

BACKGROUND OF THE INVENTION

It is desireable or may be required by law to provide hearing protection in the form of earplugs, for persons exposed to environments where noises are generated sufficiently loud to constitute a danger to hearing.

Particularly where such hearing protection need only be intermittently used it is necessary for each individual to have such protection conveniently and readily available on their person. Because of the resiliency of most earplugs, it is important to have a relatively rigid member available to fit into or be adapted to holding the earplug for insertion into the ear. Such inserters have been associated with the container for the plugs, as shown in U.S. Pat. No. 2,393,340. A different design which has been made is shown in abandoned U.S. application No. 681,164 filed Apr. 28, 1976, which includes separate compartments for each earplug and a removeable cover drawing oppositely directed male type and female type inserters formed thereon.

SUMMARY OF THE INVENTION

The container-inserter of the present invention is provided with a pivotable cap or cover which locks closed by a resilient detent and rotates about one end to open the container. Fixed on one end of the cover are oppositely directed inserter means. When open, by rotation of 90°, the cover is locked into the container to prevent its loss, and to permit the container itself to be employed as the handle to manipulating the inserter when the plug is being positioned in the ear canal. Further rotation of the cover by an additional 90° permits removal of the cover and reversal, to place the alternate inserter means in operative position, the choice of inserter type depending upon the type of earplugs being employed.

DESCRIPTION OF THE DRAWING

In the drawing, FIG. 1 is a top view of the container of the invention showing, in phantom lines, the cover rotated toward the open position.

FIG. 2 is a side view, partially broken away and in section.

FIG. 3 is a bottom view.

FIG. 4 is a top view like FIG. 1, but with the cover removed.

FIG. 5 is one end view of the cover, removed from the container showing how the inserter means fits two alternate types of earplugs.

FIG. 6 is an opposite end view of the cover showing the closing or locking means.

FIG. 7 is a partially broken away front end view of the container with the cover removed.

DETAILED DESCRIPTION OF THE INVENTION

Figure 8:
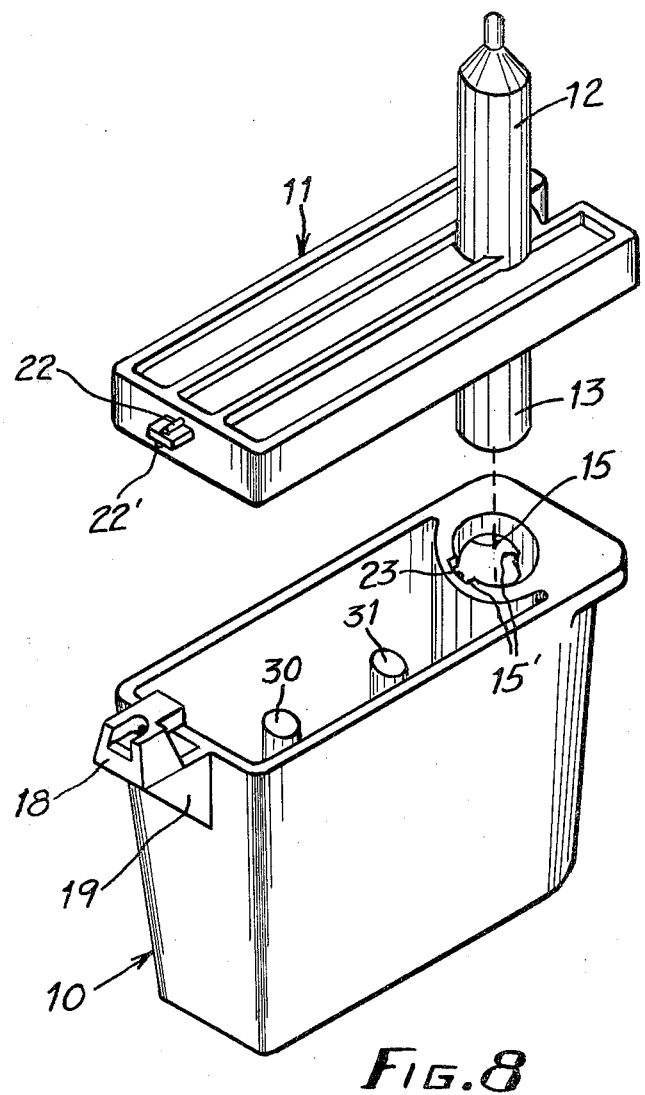
FIG. 8 is a perspective view of the container with the cover elevated above it.

The overall form of the illustrated embodiment of the invention is most clearly shown in the partially cutaway and partially sectional view of FIG. 2, in which 10 is the container and 11 is the cover member having integrally attached to it earplug inserting means 12 and 13. The outer diameter of each of the insertion members 12 and 13 is such as to snugly but rotationally fit within the collar 14 formed at one end of the container 10. The bottom surface of the collar 14 is provided with a cam surface 15 and as more clearly shown in FIG. 6 and 7. Cooperating with the cam surface 15 is boss 17 projecting from the surface of the inserter 13 in FIG. 2. When it is desired to use the inserter 13, instead of the inserter 12, the cover member 11 is reversed and boss 17' then coacts with the cam surface 15 and stops 15'.

At the front top end of container 10 is a latching bar 18, supported by vertical arms 19 and 20. A latching slot is provided at 21 in the middle of bar 18, for cooperation with detent 22 or 22' provided at the front end of cover 11.

As most clearly shown in FIG. 4, collar 14 is provided with a slot 23 for allowing entry of boss 17 or 17' when the cover 11 is assembled into the container 10.

The container 10 is shown holding earplugs 30 and 31 in FIG. 2. In FIG. 5 the male inserter member 12 is shown, for illustrative purposes only, holding a single flange type plug 32 having a recess 33 for accomodation of the inserter 12. The other inserter 13 is shown holding a triple flange earplug 34, having an extension 35 for seating in the cooperating recess of inserter member 13. In operation, the cover member 11 would be in place on the container 10, and the user would hold the container as he would the butt of a pistol for insertion of an earplug which is seated on an inserter 12 or 13.

When cover 11 is in the closed position, as shown in FIG. 2, the cover is tightly sealed against the body 10 by pressure of bar 18, and cam 15 against detent 22 and boss 17, respectively. Such tight sealing insures against entry of dust and grip into the container when the cover is in the closed position. The parts 10 and 11 are suitably made of a resilient plastic material such as polyethylene.

When it is desired to entirely remove the cover 11 (when it is, for example, desired to reverse the position so as to employ the alternate insertion device) the cover is rotated, as shown in the phantom lines in FIG. 2, a full 180° from the closed position. In that position the detent 17 or 17' prevents further rotation, being against the vertical end surface 15' of the cam 15 and is lined up with the slot 23 in collar 14. The cover can then be pulled upwardly to free it from the container and reverse it if so desired.

What is claimed is:

1. An earplug container having a cylindrical collar in one end thereof, and a cover, said cover being adapted to pivot about said cylindrical collar, said cover having oppositely projecting male and female inserter members each having a cylindrical portion adapted to engage said cylindrical collar in said container, said collar including a recess at the bottom thereof for assembly of said cover on said container and including a cam surface, a boss on each of said cylindrical inserter adapted to pass through said recess and engage said cam surface on the bottom of said collar, said cam surface being so arranged as to urge said cover downwardly against said container when the cover is pivoted about said cylindrical collar toward its closed position, and latch means at the opposite end of said container detent means on said cover overlying said latch means, said latch cooperating with a detent on said cover to latch said cover in closed position and to urge said cover against said container.

* * * * *